United States Patent [19]

Winters et al.

[11] Patent Number: 4,530,927

[45] Date of Patent: Jul. 23, 1985

[54] ANTIINFLAMMATORY AND ANXIOLYTIC ISOXAZOLE-[5,4-B]PYRIDINES

[75] Inventors: Giorgio Winters, Milan; Alberto Sala, Monza, both of Italy

[73] Assignee: Gruppo Lepetit S.p.A., Italy

[21] Appl. No.: 479,378

[22] Filed: Mar. 28, 1983

[30] Foreign Application Priority Data

Mar. 30, 1982 [GB] United Kingdom ............... 8209361

[51] Int. Cl.³ .................. A61K 31/55; A61K 31/535; C07D 498/04; C07D 498/14
[52] U.S. Cl. ................ 514/215; 260/244.4; 514/234; 514/253; 514/293; 544/126; 544/361; 546/83
[58] Field of Search ................ 546/83; 544/126, 361; 424/258, 256, 250, 248.55, 248.57; 260/244.4

[56] References Cited

U.S. PATENT DOCUMENTS 3,541,101  11/1970  Markillie ........................ 546/83
3,816,429   6/1974  Finch .............................. 546/83
4,113,731   9/1978  Winters et al. ............... 546/83 X

*Primary Examiner*—Richard A. Schwartz
*Attorney, Agent, or Firm*—William J. Stein; Stephen L. Nesbitt; Gary D. Street

[57] ABSTRACT

New isoxazole[5,4-b]pyridines having antiinflammatory, CNS-depressant and cardiovascular activity.

3 Claims, No Drawings

ANTIINFLAMMATORY AND ANXIOLYTIC ISOXAZOLE-[5,4-B]PYRIDINES

The present invention refers to new isoxazole-[5,4-b]-pyridines of the formula

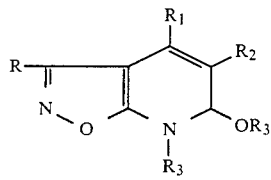

wherein R represents a lower alkyl group of 1-4 carbon atoms or phenyl or halophenyl; $R_1+R_2$ represents an alkylene group $—(CH_2)_n—$ wherein n is an integer from 3 to 5 included and one of the methylene groups may be replaced by a group $=NR_6$ in which $R_6$ represents lower alkyl, lower alkanoyl or (lower alkoxy)carbonyl; $R_3$ is present only once and represents hydrogen, lower alkyl, hydroxy-lower alkyl, benzyl and, if it is bound to the heterocyclic nitrogen, also halo-lower alkyl or amino-lower alkyl in which the amino nitrogen may be dialkyl substituted or be included in a saturated heterocyclic ring; the dashed line indicates that a double bond is present either between the heterocyclic nitrogen atom and the ring carbon atom, or between the oxygen and the ring carbon atom, in the first case the radical $R_3$ being bound to the oxygen, in the second case to the nitrogen atom.

As used herein the term "lower alkyl" represents straight or branched ($C_1$-$C_6$)alkyl groups such as methyl, ethyl, propyl, isopropyl, n-butyl, sec-butyl, tert.butyl and so on; the term "lower alkoxy" represents straight or branched ($C_1$-$C_6$)alkoxy groups such as methoxy, ethoxy, propoxy, iso-propoxy, n.butoxy, t.butoxy and the like; the term "lower alkanoyl" represents straight or branched ($C_1$-$C_6$)alkanoyl groups such as acetyl, propanoyl, butanoyl and the like. The compounds of the invention, as well as many intermediates for their synthesis which will be hereinafter described, possess antiinflammatory, cardiovascular and CNS depressant activity.

The general method for preparing the compounds of the invention starts from a 3-substituted 5-aminoisoxazole I which is reacted with a cyclic ketone II to form a 3,4-disubstituted 5-aminoisoxazole III.

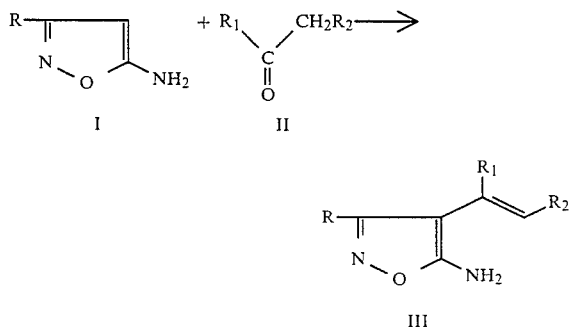

In these formulas R, $R_1$ and $R_2$ have the above mentioned significances. The reaction is best carried out in a lower carboxylic acid, preferably acetic acid as a solvent, at a temperature ranging between room temperature and the boiling temperature of the solvent, preferably at 40°-70° C. The molar ratio between the two reactants varies depending on the nature of the reactant. It was found that usually an excess over 1 mole of the cyclic ketone per mole of isoxazole, up to 3 moles, gives good results. The reaction time may vary within wide ranges and depends largely on the used temperature. In some cases 3-4 hours are sufficient to have a complete reaction, while sometimes a time of $24 \geqq 36$ hours may be appropriate.

Compound III, when treated with a lower alkyl isocyanate gives an isoxazole[5,4-b]-pyridone V, which, when treated with an alkali hydride and then with an alkylating agent, gives a mixture of O- and N-substituted isoxazolo-[5,4-b]-pyridines VI and VII

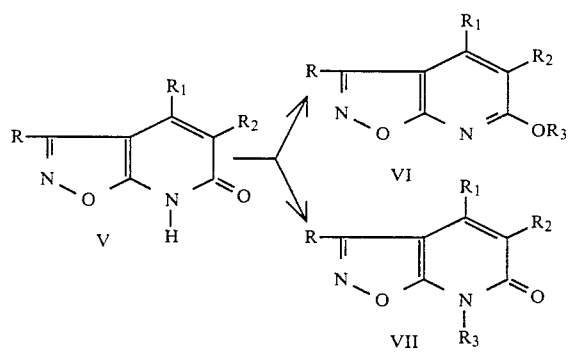

In all these formulas R, $R_1$ and $R_2$ have the above mentioned meanings. On the contrary, $R_3$ only represents hydrogen, lower alkyl, hydroxy-lower alkyl and benzyl.

The conversion of III into V is best carried out by heating III with the lower alkyl isocyanate using as a solvent a tertiary base, such as triethylamine or pyridine, at the boiling temperature of the solvent for 1-6 hours. The intermediate urea IV is formed during the reaction, but gradually it gives V in high yields.

For converting V into the mixture of VI and VII, compound V is first treated with sodium hydride in an anhydrous solvent, thus obtaining the sodium salt, which is heated in the same solvent at 40°-80° C. for 1-3 hours. The compounds VI and VII are formed in variable mutual ratio depending on the reaction conditions. By selecting case by case the most appropriate reaction conditions it is largely possible to pilot the reaction toward the preferential formation of VI or VII.

When compounds of formula VII are desired in which $R_3$ means halo-lower alkyl or amino-lower alkyl where the amino nitrogen may be dialkyl substituted or be included in a saturated heterocyclic ring, either compound VI or compound VII or their mixtures, in which $R_3$ means hydroxy-lower alkyl, are first converted into the corresponding halo-lower alkyl derivatives, and these latter into the amino-lower alkyl derivatives through processes well known to all those skilled in the art. It is to be pointed out that use, alone or in mixture, of compound VI as the starting compound of this reaction step involves a rearrangement of the chloro-lower alkyl group from the oxygen to the nitrogen atom through formation of a cyclic intermediate:

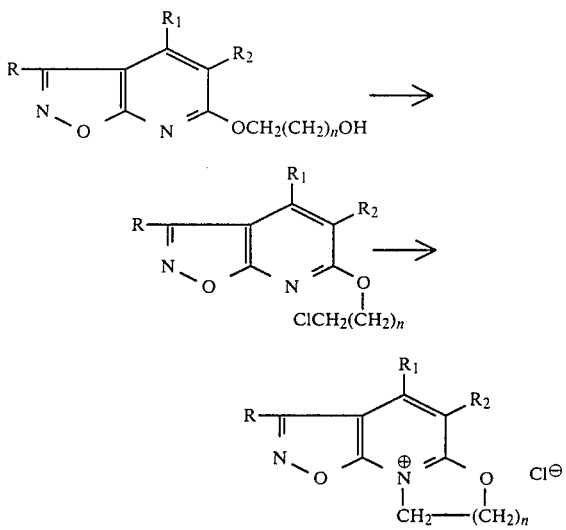

whereby in any case the end compound has the substituent $R_3$ bound to the heterocyclic nitrogen atom. In the actual practice, compound VI or compound VII or their mixtures, in which $R_3$ is a hydroxy-lower alkyl group, are dissolved or suspended in a suitable organic solvent such as, for instance, a $C_1$-$C_4$ halogenated hydrocarbon and a molar excess of a halogenating agent, preferably from about 1 to about 3 molar equivalents, are added. Although substantially all of the common halogenating agents act satisfactorily, the best results are normally obtained by employing thionyl halides, e.g. thionyl chloride or thionyl bromide, at a temperature ranging between room temperature and about 70° C., and is completed with 1-4 hours.

The amino-lower alkyl derivatives are then prepared by obvious procedure, for instance by treating the chloroalkyl derivative with a base under conditions which are generally known to all those skilled in the art and which will be apparent from the appended examples. As stated above, the compounds of the invention possess interesting CNS-depressant, anti-anxiety and antiinflammatory activity. Moreover, they display a considerably low toxicity as, generally, their $LD_{50}$ values are higher than 500 mg/kg when given intraperitoneally and rarely lower than 1000 mg/kg. when given orally to mice. The antiinflammatory action was ascertained by means of the "carrageenin induced edema test" in rats. Said test was performed according to the operative scheme proposed by C. A. Winter et al., Proc. Soc. Exptl. Biol. Med., 111, 544, 1962 and it was found that oral dosages comprising between about 1/5 and about 1/10 of the $LD_{50}$ values of the compounds of Example 5 a, 21, 22 and 24 (N-isomers) are able to cause a significant reduction of the edema of 35% or more over the control.

The CNS-depressant activity was investigated by means of the general psychophysic screening method, as described by S. Irwin in Psychopharmacologia (Berl). 13, 222-257, 1968. In particular, some representative experiments carried out on mice have shown that amounts from about 5 to about 100 mg/kg. i.p. of the compounds were effective in inhibiting the spontaneous activity and the muscular tone, whereas amounts from about 30 to about 300 mg/kg. i.p. significantly impaired the motor coordination and the righting reflex of the laboratory animals. It is to be noted that the above parameters are directly connected to sedative, hypnotic and myorelaxing properties. The antianxiety activity of the compounds of the invention was investigated by means of the "pole climbing avoidance test", performed as described by G. Maffii in Journ. Pharm.Pharmacol.,11, 129, 1959, wherein a conditioned animal (generally rat) is deconditioned i.e., is brought to its normal psychic behavior by administration of a suitable amount of the compound to be tested. According to G. Maffii, an inhibition of the secondary conditioned response ($CR_2$) without a contemporary or coupled with an insignificant inhibition of the primary conditioned response (CR) and the unconditioned response (UR) is a clear indication of an antianxiety effect since these last two parameters are connected with sedative and hypnotic properties.

Representative experiments carried out on groups of ten rats have shown that dosages varying from about 15 to about 60 mg/kg. of body weight administered i.p. of the compounds of Examples 1b. 4a, 12a, 25 (o-isomer) and 42 (o-isomer) are highly effective in inhibiting the $CR_2$— parameter and, contemporaneously, have practically no influence on the CR and the UR.

The compounds of the invention may be administered by different routes. While the preferred routes of administration are oral and rectal, parenteral administration can also be employed. For oral administration, the compounds are compounded into pharmaceutical dosage forms, such as, for instance, tablets capsules, elixirs, solutions and the like. The dosage unit may contain the usual excipients, e.g. starch, gums, fatty acids, alcohols, sugars, etc. For rectal administration the compounds are administered in the form of suppositories, admixed with conventional vehicles, such as, for example, cocoa butter, wax, spermaceti or polyoxyethyleneglycols and their derivatives.

The dosage range is from about 0.05 to about 2.00 g. per day, preferably administered in divided dose. Accordingly the present invention provides a therapeutic composition comprising as the active ingredient a compound of the invention together with a pharmaceutically acceptable carrier.

The following additional description and examples further describe the invention and the manner and process of making and using it to enable the art skilled to make and use the same and set forth the best mode contemplated by the inventors of carrying out the invention.

EXAMPLE 1

6,7,8,9-Tetrahydro-1-methylisoxazole-[5,4-c]-isoquinoline-5(4H)-one.

(a) To a solution of 5-amino-3-methylisoxazole (17 g.) in acetic acid (170 ml.), 35 ml. of cyclohexanone are added and the mixture is heated at 70° C. for 17 hours. The acetic acid is distilled in vacuo, the residue is dissolved in ethyl acetate, the solution washed with a saturated aqueous solution of sodium bicarbonate and then with water, dried over anhydrous sodium sulfate and evaporated to dryness. The crude product may be used as such for the following step. It may be obtained by chromatography on $SiO_2$ and elution with a mixture n-hexane: ethyl acetate 9:1.Yield 26 g. (84%) of 4-(1- cyclohexen-1-yl)-3-methyl-5-isoxazoleamine (from diethyl ether). M.p. 48° C.

(b) A mixture of crude 4-(1-cyclohexen-1-yl)-3-methyl-5-isoxazoleamine (9.5 g.), 95 ml. of pyridine and 15.8 ml. of ethyl isocyanate is refluxed for 3 hours, then the solvent is distilled off in vacuo. The residue is refluxed for some minutes with a few milliliters of ethyl acetate and after cooling the formed pure 6,7,8,9-tetrahydro-1-methylisoxazole-[5,4-c]-isoquinoline-5(4H)-one is collected on filter and dried. After recrystallization from dimethylformamide/methanol the product has m.p. 255° C. When starting from pure intermediate yields of 88-92% calculated on the intermediate were obtained.

EXAMPLES 2-14

(a) Isoxazolamines.

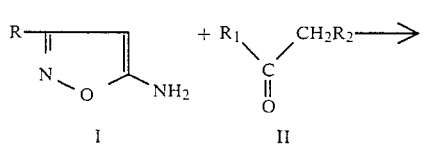

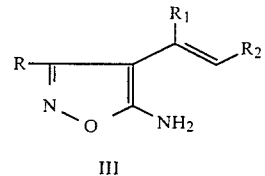

III

Starting from an oxazolamine of formula I and a ketone of formula II, the following compounds of formula III were prepared by processes substantially identical with that described in Example 1(a).

| Example | R | $R_1 + R_2$ | yield % | M.p. °C. |
|---|---|---|---|---|
| 2a | $C_6H_5$— | —$(CH_2)_3$— | 55 | oil |
| 3a | $C_6H_5$— | —$(CH_2)_4$— | 69 | 156–158 |
| 4a | $C_6H_5$— | —$(CH_2)_2N(CH_3)CH_2$— | 86 | 185–186 |
| 5a | $C_6H_5$— | —$(CH_2)_2N(COCH_3)CH_2$— | 87 | 158–161 |
| 6a | 4-$ClC_6H_4$— | —$(CH_2)_4$— | 79 | 163–164 |
| 7a | 4-$ClC_6H_4$— | —$(CH_2)_2N(CH_3)CH_2$— | 85 | 188–190 |
| 8a | $CH_3$— | —$(CH_2)_5$— | 61 | oil |
| 9a | $CH_3$— | —$(CH_2)_2N(CH_3)CH_2$— | 78 | 126–127 |
| 10a | $CH_3$— | —$(CH_2)_2N(COCH_3)CH_2$— | 88 | 227–229 |
| 11a | $CH_3$— | —$(CH_2)_3$— | 40 | 84–86 |
| 12a | i-$C_3H_7$— | —$(CH_2)_4$— | 65 | 115–116 |
| 13a | i-$C_3H_7$— | —$(CH_2)_2N(COCH_3)CH_2$— | 70 | 173–174 |
| 14a | $CH_3$ | —$CH_2$—$N(COOC_2H_5)CH_2CH_2$— | | 126–127 |

(b) Isoxazole-isoquinolines

Starting from the above obtained isoxazolamines III, and working substantially as described in Example 1(b), the following compounds of formula V were prepared

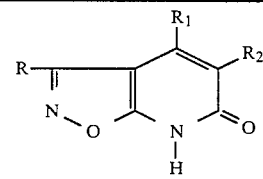

V

| Example | R | $R_1 + R_2$ | yield % | M.p. °C. |
|---|---|---|---|---|
| 2b | $C_6H_5$— | —$(CH_2)_3$— | 81 | dec 230 |
| 3b | $C_6H_5$— | —$(CH_2)_4$— | 82 | 228–229 |
| 4b | $C_6H_5$— | —$(CH_2)_2N(CH_3)CH_2$— | 80 | dec 264–265 |
| 5b | $C_6H_5$— | —$(CH_2)_2N(COCH_3)CH_2$— | 83 | dec 235 |
| 6b | 4-$ClC_6H_4$— | —$(CH_2)_4$— | 91 | dec 250 |
| 7b | 4-$ClC_6H_4$— | —$(CH_2)_2N(CH_3)CH_2$— | 83 | dec 246–248 |
| 8b | $CH_3$— | —$(CH_2)_5$— | 67 | 226–227 |
| 9b | $CH_3$— | —$(CH_2)_2N(CH_3)CH_2$— | 83 | dec 270 |
| 10b | $CH_3$— | —$(CH_2)_2N(COCH_3)CH_2$— | 83 | 259–261 |
| 11b | $CH_3$— | —$(CH_2)_3$— | 54 | 239–242 |
| 12b | i-$C_3H_7$— | —$(CH_2)_4$— | 80 | 225–227 |
| 13b | i-$C_3H_7$— | —$(CH_2)_2N(COCH_3)CH_2$— | 95 | 245–246 |
| 14b | $CH_3$— | —$(CH_2)_2$—$N(COOC_2H_5)CH_2$— | | 225–226 |

EXAMPLE 15

6,7,8,9-Tetrahydro-1-methyl-5-propoxyisoxazole-[5,4-c]-isoquinoline and
6,7,8,9-tetrahydro-1-methyl-4-propylisoxazole-[5,4-c]-isoquinoline-5-(4H)-one.

To a stirred suspension of 22.5 g. of 6,7,8,9-tetrahydro-1-methylisoxazole-[5,4-c]-isoquinoline-5(4H)-one in anhydrous dimethylformamide (600 ml.), 5,81 g. of a 50 percent suspension of sodium hydride in mineral oil is added at small portions at 20° C. under a nitrogen atmosphere. The mixture is heated at 70° C. for 1 hour, then cooled to 15° C. and 15 ml. of propyl bromide in 50 ml.

of dimethylformamide are dropped in. Heating at 70° C. is continued for 2.5 hours, the solvent is evaporated in vacuo and the residue is added with methylene chloride and water. The organic layer is separated, the aqueous layer is washed with methylene chloride and the combined organic solutions are washed with water to neutral reaction. The solvent is evaporated in vacuo. The formed isomeric mixture (26 g.) is separated by chromatography on silica gel (400 g.) eluting with methylene chloride and ethyl acetate. The less polar product, i.e. the 5-propoxy derivative, crystallized from ethyl ether/hexane, has m.p. 97°–98° C. Yield 12.3 g. The more polar product, i.e. the 4-propyl derivative, crystallized from ethyl ether/hexane, has m.p. 82°–83° C. Yield 11.8 g.

EXAMPLES 16–44

By processes substantially identical with that of example 15 the following compounds of formulas VI and VII were prepared

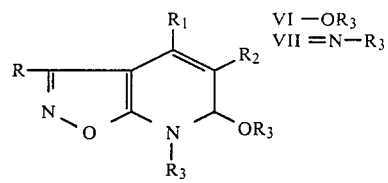

VI —OR$_3$
VII =N—R$_3$

| Example | formula | R | R$_1$ + R$_2$ | R$_3$ | yield % | m.p. °C. |
|---|---|---|---|---|---|---|
| 16 | VI | C$_6$H$_5$— | —(CH$_2$)$_4$— | CH$_3$— | 21.6 | 167 |
|    | VII | " | " | " | 58.4 | 158 |
| 17 | VI | " | " | CH$_3$(CH$_2$)$_3$— | 56 | 64–65 |
|    | VII | " | " | " | 39 | 117 |
| 18 | VI | " | " | C$_6$H$_5$CH$_2$— | 40.5 | 144–145 |
|    | VII | " | " | " | 49.5 | 196–198 |
| 19 | VI | " | " | HOCH$_2$CH$_2$— | 26 | 108–109 |
|    | VII | " | " | " | 46 | 204–205 |
| 20 | VI | 4-ClC$_6$H$_4$— | " | " | 23.5 | 167–168 |
|    | VII | " | " | " | 60.5 | 224–225 |
| 21 | VI | CH$_3$ | " | CH$_3$ | 17.2 | 162–163 |
|    | VII | " | " | " | 61.6 | 139–144 |
| 22 | VI | " | " | C$_2$H$_5$— | 48 | 146–147 |
|    | VII | " | " | " | 44 | 104–105 |
| 23 | VI | " | " | (CH$_3$)CH— | 76.5 | 91–92 |
|    | VII | " | " | " | 9.5 | 113–114 |
| 24 | VI | " | " | HOCH$_2$CH$_2$— | 28 | 157–159 |
|    | VII | " | " | " | 60 | 163–164 |
| 25 | VI | " | " | HO(CH$_2$)$_3$— | 27 | 106–107 |
|    | VII | " | " | " | 35 | 123–124 |
| 26 | VI | " | —(CH$_2$)$_5$— | HOCH$_2$CH$_2$— | 18 | 125–126 |
|    | VII | " | " | " | 51 | 170–171 |
| 27 | VI | " | —(CH$_2$)$_2$N(CH$_3$)CH$_2$— | " | 12 | 154–156 |
|    | VII | " | " | " | 35 | 178–179 |
| 28 | VI | " | —(CH$_2$)$_2$N(COCH$_3$)CH$_2$— | CH$_3$— | 19.5 | 150–151 |
|    | VII | " | " | " | 55.5 | 183–185 |
| 29 | VI | " | " | (CH$_3$)$_2$CH— |  | 136–137 |
|    | VII | " | " | " |  |  |
| 30 | VI | " | " | HOCH$_2$—CH$_2$— | 4.5 | not isolated |
|    | VII | " | " | " | 90 | 209–211 |
| 31 | VI | " | —(CH$_2$)$_4$— | CH$_3$(CH$_2$)$_3$— | 51.3 | 96–97 |
|    | VII | " | " | " | 43.7 | 52–53 |
| 32 | VI | " | " | CH$_3$(CH$_2$)$_5$— | 56.5 | 76–77 |
|    | VII | " | " | " | 37.5 | b.p. 190/93 mm |
| 33 | VI | " | —(CH$_2$)$_5$— | C$_2$H$_5$— | 58 | 111–113 |
|    | VII | " | " | " | 36 | 109–110 |
| 34 | VI | " | " | (CH$_3$)$_2$CH— | 82 | 99–100 |
|    | VII | " | " | " | 6 | 96–98 |
| 35 | VI | " | —(CH$_2$)$_3$— | C$_2$H$_5$— | 57 | 106–107 |
|    | VII | " | " | " | 36.5 | 107–108 |
| 36 | VI | " | " | (CH$_3$)$_2$CH— | 76.5 | 84–85 |
|    | VII | " | " | " | 7.5 | 133–134 |
| 37 | VI | " | —(CH$_2$)$_2$—N(COO$_2$H$_5$)CH$_2$— | C$_2$H$_5$— |  | 127–128 |
|    | VII | " | " | " |  | 110–111 |
| 38 | VI | " | " | (CH$_3$)$_2$CH— |  | 114–115 |
|    | VII | " | " | " |  | 106–108 |
| 39 | VI | (CH$_3$)$_2$CH— | —(CH$_2$)$_4$— | C$_2$H$_5$— | 53.5 | 132–133 |
|    | VII | " | " | " | 38.5 | 102–103 |
| 40 | VI | " | " | (CH$_3$)$_2$CH— | 82 | 66–67 |
|    | VII | " | " | " | 7 | 72–73 |
| 41 | VI | " | —(CH$_2$)$_2$N(COCH$_3$)CH$_2$— | C$_2$H$_5$— | 53.5 | 137–138 |
|    | VII | " | " | " | 40.5 | 138–139 |
| 42 | VI | " | " | CH$_3$(CH$_2$)$_3$— | 56.5 | 108–110 |
|    | VII | " | " | " | 39.5 | 115–117 |
| 43 | VI | " | " | (CH$_3$)$_2$CH— |  | 119–120 |
|    | VII | " | " | " |  |  |
| 44 | VI | —CH$_3$ | —(CH$_2$)$_2$N(COCH$_3$)CH$_2$— | C$_2$H$_5$— |  | 155–156 |

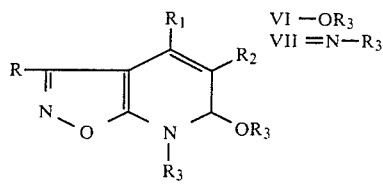

| Example | formula | R | R₁ + R₂ | R₃ | yield % | m.p. °C. |
|---|---|---|---|---|---|---|
|  | VII | " | " | " |  | 151–152 |

Additional illustrations of possible variations of the procedure for Example 24 are hereinafter described in full. To a stirred suspension of 20.4 g of 6,7,8,9-tetrahydro-1-methylisoxazole-[5,4-c]-isoquinoline-5(4H)-one, prepared according to Example 1b, in 550 ml of anhydrous dimethylformamide 3.3 g of a 80 percent suspension of sodium hydride are added at small portions at 20° C. under nitrogen. After heating 1 hour at 70° C. the mixture is cooled to 15° C. and 8 ml. of 2-bromoethanol in 50 ml. of dimethylformamide are dropped in. The mixture is heated 3 hours at 70° C., the solvent is evaporated in vacuo and the residue extracted with methylene chloride. the organic solvent is washed with water, dried over sodium sulfate and evaporated to dryness in vacuo. By recrystallization of the residue from ethyl acetate 8 g. of 6,7,8,9-tetrahydro-1-methyl-4-hydroxyethylisoxazole-[5,4-c]-isoquinoline-5(4H)-one are obtained. M.P. 163°–164° C.

From the mother liquor by chromatography on 400 g. of silica gel and eluting with hexane and ethyl acetate, 7 g. of 6,7,8,9-tetrahydro-1-methyl-5-(2-hydroxyethoxy)-isoxazole-[5,4-c]-isoquinoline-5(4H)-one are obtained. M.p. 157°–159° C.

A further crop of the 4-hydroxyethyl derivative (6.7 g.) is obtained from the last fraction of the chromatography.

EXAMPLE 45

6,7,8,9-Tetrahydro-1-methyl-4-(2-chloroethyl)-isoxazole-[5,4-c]-isoquinoline-5(4H)-one. To a stirred solution, cooled to 0° C., of 12 g. of the mixture obtained according to Example 24 before separation of the two isomers, in 200 ml. of methylene chloride, a solution of 6.96 ml. of thionyl chloride in 30 ml. of methylene chloride is added dropwise. After 2 hours at 20° C. the solvent is removed in vacuo and diethyl ether is added to the residue. The solid is collected and represents substantially pure 6,7,8,9-tetrahydro-1-methyl-4-(2-chloroethyl)-isoxazole-[5,4-c]-isoquinoline-5(4H)one. Yield 12 g. (94%). An analytically pure sample may be obtained by recrystallization from ethyl acetate. M.p. 161°–162° C.

EXAMPLES 46–50

By processes substantially identical with that of Example 45 the following compounds of formula VIII were prepared

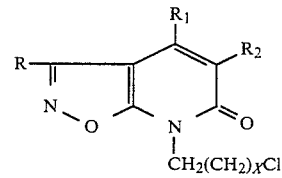

| Example | R | R₁ + R₂ | X | yield % | M.p. °C. |
|---|---|---|---|---|---|
| 46 | C₆H₅— | —(CH₂)₄— | 1 | 90 | 120–121 |
| 47 | 4-Cl—C₆H₅— | " | 1 | 95 | 177–179 |
| 48 | CH₃ | " | 2 | 87 | 102–103 |
| 49 | " | —(CH₂)₅— | 1 | 70 | 153–154 |
| 50 | " | —(CH₂)₂N(COCH₃)CH₂— | 1 | 81 | 145–146 |

EXAMPLE 51

6,7,8,9-Tetrahydro-1-methyl-4-[2-(1-morpholinoethyl)]-i-soxazole-[5,4-c]-isoquinoline-5(4H)-one.

A suspension of 7 g. of the N-chloroethyl compound prepared according to Example 45 in 35 ml. of morpholine is refluxed under nitrogen for 1.5 hours. After distilling the excess morpholine in vacuo, ethyl acetate is added to the residue, the organic solution is washed with water, dried over sodium sulfate and evaporated to dryness in vacuo. By chromatography on 140 g. of silica gel and elution with hexane:ethyl acetate 2:8 mixture the title compound is obtained. Yield 4.8 g. (54%). The hydrochloride, prepared as usual by precipitating it from an organic solution with hydrogen chloride, when recrystallized from ethanol has m.p. 190° C. (dec.).

EXAMPLES 52–56

By processes substantially identical with that of Example 51, except that occasionally a solvent like ethanol or dimethylformamide was used in place of the solvent/reagent morpholine of Example 51 the following compounds of formula IX were prepared.

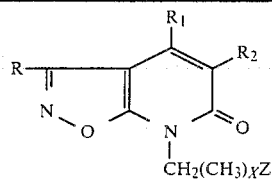

| Example | R | $R_1 + R_2$ | X | Z | yield % | M.p. °C. |
|---|---|---|---|---|---|---|
| 52 | $CH_3$ | $-(CH_2)_4-$ | 1 | $-N(C_2H_5)_2 \cdot HCl$ | 39 | 158–160 |
| 53 | " | " | 1 | $-NCH_2CH_2N(CH_3)CH_2CH_2$ | 33 | 142–143 |
| 54 | " | " | 1 | $-NCH_2CH_2N(C_6H_5)CH_2CH_2$ | 44 | 150–151 |
| 55 | " | " | 2 | $-NCH_2CH_2OCH_2CH_2 \cdot HCl$ | 57 | 210 dec. |
| 56 | " | $-(CH_2)_5-$ | 1 | $-NCH_2CH_2N(C_6H_5)CH_2CH_2$ | 37 | 155–157 |

We claim:

1. An isoxazole pyridine having the formula

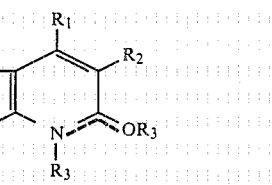

wherein R represents a lower alkyl group of 1–4 carbon atoms or phenyl or halophenyl; $R_1+R_2$ represent an alkylene group $-(CH_2)_n-$ wherein n is an integer from 3 to 5 included and one of the methylene groups may be replaced by a group $=NR_6$ in which $R_6$ represents lower alkyl, lower alkanoyl or (lower alkoxy)carbonyl; $R_3$ is present only once and represents hydrogen, lower alkyl, hydroxy-lower alkyl, benzyl and, if it is bound to the heterocyclic nitrogen, also halo-lower alkyl or amine-lower alkyl in which the amino nitrogen may be dialkyl substituted or be included in a saturated heterocyclic ring, selected from the group consisting of N-methylpiperazino, N-phenylpiperazino and morpholino; the dashed line indicates that a double bond is present either between the heterocyclic nitrogen atom and the ring carbon atom, or between the oxygen and the ring carbon atom, in the first case the radical $R_3$ being bound to the oxygen, in the second case to the nitrogen atom.

2. An antiinflammatory, anxiolytic or cardiovascular composition comprising a therapeutically effective amount of a compound of claim 1 as the active ingredient and a pharmaceutically acceptable carrier.

3. A method of reducing inflammation or anxiety in a patient in need thereof which comprises the daily administration of from 0.05 to 2.0 gm of a compound of claim 1.

* * * * *